(12) United States Patent
Hashimoto et al.

(10) Patent No.: US 7,285,668 B2
(45) Date of Patent: *Oct. 23, 2007

(54) PROCESS FOR THE CRYSTALLIZATION OF (R)- OR (S)-LANSOPRAZOLE

(75) Inventors: Hideo Hashimoto, Kobe (JP); Tadashi Urai, Kawanishi (JP)

(73) Assignee: Takeda Pharmaceutical Company Limited, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 10/432,798

(22) PCT Filed: Nov. 30, 2001

(86) PCT No.: PCT/JP01/10462

§ 371 (c)(1),
(2), (4) Date: May 27, 2003

(87) PCT Pub. No.: WO02/44167

PCT Pub. Date: Jun. 6, 2002

(65) Prior Publication Data

US 2004/0049045 A1    Mar. 11, 2004

(30) Foreign Application Priority Data

Dec. 1, 2000  (JP) .............................. 2000-367757

(51) Int. Cl.
C07D 401/12 (2006.01)

(52) U.S. Cl. .................................. 546/273.7

(58) Field of Classification Search ............. 546/273.7; 514/338
See application file for complete search history.

(56) References Cited

U.S. PATENT DOCUMENTS

| | | | | |
|---|---|---|---|---|
| 6,002,011 A | * | 12/1999 | Kato et al. ................ | 546/273.7 |
| 6,462,058 B1 | * | 10/2002 | Fujishima et al. .......... | 514/338 |
| 6,608,092 B1 | * | 8/2003 | Fujishima et al. .......... | 514/338 |
| 6,664,276 B2 | * | 12/2003 | Fujishima et al. .......... | 514/338 |

FOREIGN PATENT DOCUMENTS

| | | |
|---|---|---|
| EP | 0174726 | 3/1986 |
| EP | 0302720 | 2/1989 |
| EP | 1277752 | 1/2003 |
| EP | 1293507 | 3/2003 |
| WO | WO96/02535 | 2/1996 |
| WO | WO97/02261 | 1/1997 |
| WO | WO98/21201 | 5/1998 |
| WO | 9938512 | * 5/1999 |
| WO | WO 00/78745 | 12/2000 |
| WO | WO 01/14366 | 3/2001 |

OTHER PUBLICATIONS

Kotar et al. (Eur. J of Pharm Sci., 4 (1996), p. S182.*
Brittain, H.G., Polymorphism in Pharmaceutical Soldis-Drugs and the Pharmaceutical Sciences, 95, 1999, pp. 126-358.*
Chemical & Engineering News, Feb. 2003, pp. 32-35.*
Halbein et al., Journal of Pharmaceutical Sciences, 58 (1969) pp. 911-928.*
US Pharmacopia, 1995, pp. 1843-1844.*
Concise Encyclopedia Chemistry, pp. 872-873 (1993).*
Muzaffar et al., "Polymorphism and Drug, etc.," J of Pharmacy (Lahore), 1979, 1(1), 59-66.*
Jain et al., "Polymorphism in Pharmacy", Indian Drugs, 1986, 23(6), 315-329.*
Doelker et al., CA 132:325872 (1999).*
Taday et al., "Using Terahertz, etc.," J of Pharm. Sci., 92(4), 2003, 831-838.*
Otsuka et al., "Effect of Polymorphic, etc.," Chem. Pharm. Bull. 47(6) 852-856 (1999).*
Ulicky et al., Comphrehensive Dictionary, etc., NY: Prentice Hall, 1992, 21.*
Brittain et al., "Polymorphism in Pharmaceutical Solids", NY: Marcel Dekker et al., (1999), pp. 1-2, 125-181, 183-226, 228-278.*

* cited by examiner

*Primary Examiner*—Patricia L. Morris
(74) *Attorney, Agent, or Firm*—Hamre, Schumann, Mueller & Larson, PC (57) ABSTRACT

The present invention relates to a production method of a crystal of (R)-lansoprazole or (S)-lansoprazole, which includes crystallization at a temperature of about 0° C. to about 35° C. from a $C_{1-4}$ alkyl acetate solution containing (R)-lansoprazole or (S)-lansoprazole at a concentration of about 0.1 g/mL to about 0.5 g/mL and the like. According to the production method of the present invention, a crystal of (R)-lansoprazole or (S)-lansoprazole superior in preservation stability can be produced efficiently on an industrial large scale.

13 Claims, 1 Drawing Sheet

FIG. 1

Initial   40°C   50°C   60°C      Initial   40°C   50°C   60°C
        2W     2W     2W                    2W     2W     2W Method of present invention      Conventional method (melting start temperature: about 134°C)      (melting start temperature: about 130°C)

PROCESS FOR THE CRYSTALLIZATION OF (R)- OR (S)-LANSOPRAZOLE

This application is the National Phase filing of International Patent Application No. PCT/JP01/10462, filed 30 Nov. 2001.

TECHNICAL FIELD

The present invention relates to production methods of an optically active sulfoxide compound having an antiulcer activity, a crystal of an optically active sulfoxide compound having remarkably improved stability, and the like.

BACKGROUND ART

As a method for producing (R)-2-[[[3-methyl-4-(2,2,2-trifluoroethoxy)-2-pyridinyl]methyl]sulfinyl]-1H-benzimidazole [hereinafter sometimes to be referred to as (R)-lansoprazole] or (S)-2-[[[3-methyl-4-(2,2,2-trifluoroethoxy)-2-pyridinyl]methyl]sulfinyl]-1H-benzimidazole [hereinafter sometimes to be referred to as (S)-lansoprazole] having an antiulcer activity, for example, JP-A-11-508590 (WO 97/02261) describes a method for optically purifying a compound product adjusted to contain an enriched enantiomer and crystallization method by removing the solvent, which comprises treating a compound containing either (+)-enantiomer or (−)-enantiomer in a greater amount, namely, a compound enriched in one enantiomer, with a solvent, selectively precipitating a racemic compound from the solvent utilizing the crystallinity of the racemate, filtering off the precipitated racemic compound and removing the solvent to give a single enantiomer of the compound having an increased optical purity, which corresponds to lansoprazole and the like.

JP-A-10-504290 (WO 96/02535) describes a production method of an optically active sulfoxide compound, which comprises subjecting a thio compound to an oxidation reaction, and crystallization (Example 11) of omeprazole, which comprises concentrating an acetonitrile solution and the like.

Lansoprazole is now on the market worldwide as a pharmaceutical product having a superior antiulcer activity. The crystal of lansoprazole is a racemate and is superior in preservation stability.

A crystal of optically active (R)-lansoprazole and (S)-lansoprazole obtained according to the above-mentioned conventional method does not necessarily satisfy the preservation stability, with the undeniable possibility of decreased purity, increased amounts of analogous materials, coloring and the like during preservation.

Therefore, there is a demand for a production method of the crystal of (R)-lansoprazole or (S)-lansoprazole sufficiently superior in the preservation stability.

DISCLOSURE OF INVENTION

As a result of various studies of the production methods of crystals of (R)-lansoprazole and (S)-lansoprazole, the present inventors have unexpectedly found for the first time that crystallization of (R)-lansoprazole and (S)-lansoprazole under specific conditions produces an extremely stable crystal and that this method is sufficiently satisfactory on an industrial scale, and completed the present invention.

Accordingly, the present invention provides the following:

[1] a method for producing a crystal of (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole, which comprises crystallizing at a temperature of about 0° C. to about 35° C. from a $C_{1-4}$ alkyl acetate solution containing (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole at a concentration of about 0.1 g/mL to about 0.5 g/mL;

[2] a method for producing a crystal of (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole, which comprises crystallizing at a temperature of about 0° C. to about 35° C. from a $C_{1-4}$ alkyl acetate solution containing (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole at a concentration of about 0.1 g/mL to about 0.5 g/mL, and adding dropwise to the $C_{1-4}$ alkyl acetate solution, at the same temperature, $C_{5-8}$ hydrocarbon in an amount of not more than 7 times the amount of the $C_{1-4}$ alkyl acetate solution;

[3] the method of the above-mentioned [1] or [2], wherein the crystallization temperature is about 20° C. to about 30° C.;

[4] the method of the above-mentioned [1] or [2] wherein the crystallization is conducted for about 30 minutes to about 4 hours;

[5] the method of the above-mentioned [1] or [2], wherein the $C_{1-4}$ alkyl acetate is ethyl acetate or propyl acetate;

[6] the method of the above-mentioned [2], wherein the $C_{5-8}$ hydrocarbon is added in an amount of not more than 5 times the amount of the $C_{1-4}$ alkyl acetate solution;

[7] the method of the above-mentioned [2], wherein the $C_{5-8}$ hydrocarbon is heptane or hexane;

[8] the method of the above-mentioned [2], wherein the $C_{5-8}$ hydrocarbon is added dropwise over about 15 minutes to about 4 hours;

[9] a crystal of (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole produced according to the method of the above-mentioned [1] or [2];

[10] a crystal of (R)-2-[[[3-methyl-4-(2,2,2-trifluoroethoxy)-2-pyridinyl]methyl]sulfinyl]-1H-benzimidazole produced according to the method of the above-mentioned [1] or [2];

[11] a crystal of (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole having a melting start temperature of not lower than about 131° C.;

[12] the crystal of the above-mentioned [11], wherein the melting start temperature is about 135° C.;

[13] a pharmaceutical composition containing the crystal of the above-mentioned [9] or [11];

[14] the pharmaceutical composition of the above-mentioned [13], which is for the prophylaxis or treatment of digestive ulcer, gastritis, reflux esophagitis, NUD (Non Ulcer Dyspepsia), gastric cancer, gastric MALT lymphoma, upper gastrointestinal hemorrhage, ulcer caused by a nonsteroidal anti-inflammatory agent, hyperacidity and ulcer due to postoperative stress, or a disease due to *Helicobacter pylori;*

[15] a method of preventing or treating digestive ulcer, gastritis, reflux esophagitis, NUD (Non Ulcer Dyspepsia), gastric cancer, gastric MALT lymphoma, upper gastrointestinal hemorrhage, ulcer caused by a nonsteroidal anti-inflammatory agent, hyperacidity and ulcer due to postoperative stress, or a disease due to *Helicobacter pylori*, which comprises administering the crystal of the above-mentioned [9] or [11] to human;

[16] use of the crystal of the above-mentioned [9] or [11] for the production of a pharmaceutical composition for the prophylaxis or treatment of digestive ulcer, gastritis, reflux esophagitis, NUD (Non Ulcer Dyspepsia), gastric cancer, gastric MALT lymphoma, upper gastrointestinal hemorrhage, ulcer caused by a nonsteroidal anti-inflammatory agent, hyperacidity and ulcer due to postoperative stress, or a disease due to *Helicobacter pylori*;

[17] a method for stabilizing a crystal of (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole, which comprises crystallizing at a temperature of about 0° C. to about 35° C. from a $C_{1-4}$ alkyl acetate solution containing (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole at a concentration of about 0.1 g/mL to about 0.5 g/mL; and the like.

DETAILED DESCRIPTION OF THE INVENTION

The "(R)-lansoprazole" or "(S)-lansoprazole" used as a starting material in the crystal production method of the present invention can be produced according to a method known per se, such as the method described in JP-A-10-504290 (WO 96/02535) or a method analogous thereto, or the method described in the following production method 1 or 2.

(1) Production Method 1

2-[[[3-Methyl-4-(2,2,2-trifluoroethoxy)-2-pyridinyl]methyl]thio]-1H-benzimidazole and an excess amount (about 1.5-10 molar equivalents) of an oxidant (e.g., peroxide such as hydrogen peroxide, tert-butyl hydroperoxide, cumene hydroperoxide, etc.) are reacted in the presence of a catalyst for asymmetric induction (e.g., optically active diol, complex of titanium(IV) alkoxide and water, etc.), an organic solvent [e.g., alcohols such as methanol, ethanol, propanol, isopropanol etc.; aromatic hydrocarbons such as benzene, toluene, xylene etc.; ethers such as diethyl ether, diisopropyl ether, butyl methyl ether, dioxane, tetrahydrofuran etc.; esters such as ethyl acetate, methyl acetate etc.; ketones such as acetone, methyl isobutyl ketone etc.; halogenated hydrocarbons such as chloroform, dichloromethane, ethylene dichloride, carbon tetrachloride etc.; amides such as N,N-dimethylformamide etc.; sulfoxides such as dimethylsulfoxide etc.; acetic acid and the like] and a base [such as an inorganic base (e.g., alkali metal carbonates (potassium carbonate, sodium carbonate etc.), alkali metal hydroxides (sodium hydroxide, potassium hydroxide etc.), alkali metal hydrides (sodium hydride, potassium hydride etc.) etc.); an organic base such as alkali metal alkoxides (sodium methoxide, sodium ethoxide, etc.), alkali metal carboxylates (sodium acetate, etc.), amines (piperidine, piperazine, pyrrolidine, morpholine, triethylamine, tripropylamine, tributylamine, trioctylamine, diisopropylethylamine, dimethylphenylamine, etc.), pyridines (pyridine, dimethylaminopyridine, etc.) and the like; a basic amino acid (e.g., arginine, lysin, ornithine etc.) and the like], at about –20° C. to 20° C. for about 0.1 to 50 hours.

The obtained compound can be isolated by a separation and purification method known per se, such as concentration, solvent extraction, crystallization, redissolution, chromatography or a combination thereof.

(2) Production Method 2

2-[[[3-Methyl-4-(2,2,2-trifluoroethoxy)-2-pyridinyl]methyl]sulfinyl]-1H-benzimidazole is subjected to optical resolution to give an isomer.

The method of optical resolution includes a method known per se, for example, a fractional recrystallization method, a chiral column method, a diastereomer method, and so forth.

The "fractional recrystallization method" includes a method in which a salt is formed between a racemate and an optically active compound [e.g., (+)-mandelic acid, (–)-mandelic acid, (+)-tartaric acid, (–)-tartaric acid, (+)-1-phenethylamine, (–)-1-phenethylamine, cinchonine, (–)-cinchonidine, brucine, etc.], which salt is separated by fractional recrystallization etc., and, if desired, subjected to a neutralization process, to give a free optical isomer.

The "chiral column method" includes a method in which a racemate or a salt thereof is applied to a column for separation of optical isomer (chiral column). In the case of liquid chromatography, for example, optical isomers are separated by adding a racemate to a chiral column such as ENANTIO-OVM (produced by Tosoh Corporation) or the DAICEL CHIRAL series (produced by Daicel Corporation), and developing the racemate in water, a buffer (e.g., phosphate buffer), an organic solvent (e.g., hexane, ethanol, methanol, isopropanol, acetonitrile, trifluoroacetic acid, diethylamine, triethylamine, etc.), or a solvent mixture thereof. In the case of gas chromatography, for example, a chiral column, such as CP-Chirasil-DeX CB (produced by GL Science), is used to separate optical isomers.

The "diastereomer method" includes a method in which a racemate and an optically active reagent are reacted (preferably, an optically active reagent is reacted with the 1-position of the benzimidazole group) to give a diastereomer mixture, which is then subjected to ordinary separation methods (e.g., fractional recrystallization, chromatography, etc.) to obtain either diastereomer, which is subjected to a chemical reaction (e.g., acid hydrolysis, base hydrolysis, hydrogenolysis, etc.) to cut off the optically active reagent moiety, whereby the desired optical isomer is obtained. Said "optically active reagent" includes, for example, optically active organic acids such as MTPA [α-methoxy-α-(trifluoromethyl)phenylacetic acid] and (–)-menthoxyacetic acid; and optically active alkoxymethyl halides such as (1R-endo)-2-(chloromethoxy)-1,3,3-trimethylbicyclo[2.2.1]heptane and the like.

The above-mentioned 2-[[[3-methyl-4-(2,2,2-trifluoroethoxy)-2-pyridinyl]methyl]thio]-1H-benzimidazole can be produced according to the method described in JP-A-61-50978, U.S. Pat. No. 4,628,098, JP-A-10-195068, WO 98/21201 and the like or a method analogous thereto.

2-[[[3-Methyl-4-(2,2,2-trifluoroethoxy)-2-pyridinyl]methyl]sulfinyl]-1H-benzimidazole is produced by the method described in JP-A-61-50978, U.S. Pat. No. 4,628,098 etc. or a method analogous thereto.

The (R)-lansoprazole or (S)-lansoprazole produced by the above-mentioned method may be a solid (crystal, amorphous) or an oily substance and may not be isolated or purified.

The crystal of (R)-lansoprazole or (S)-lansoprazole may or may not be a hydrate.

The "hydrate" includes 0.5 hydrate to 5.0 hydrate. Among others, 0.5 hydrate, 1.0 hydrate, 1.5 hydrate, 2.0 hydrate and 2.5 hydrate are preferred. More preferred is 0.5 hydrate, 1.0 hydrate and 1.5 hydrate.

When the (R)-lansoprazole or (S)-lansoprazole obtained according to the above-mentioned method as, for example, a crystal (hereinafter sometimes to be referred to as crystal (I)) and then subjected to the crystal production method of the present invention, the method of crystallization of crystal (I) includes methods known per se, for example, crystallization from a solution, crystallization from vapor, and crystallization from a molten form.

The method of the "crystallization from a solution" include, for example, a concentration method, a slow cooling method, a reaction method (diffusion method, electrolysis method), a hydrothermal growth method, a fusing agent method, and so forth. The solvents to be used include, for example, aromatic hydrocarbons (e.g., benzene, toluene, xylene, etc.), halogenated hydrocarbons (e.g., dichloromethane, chloroform, etc.), saturated hydrocarbons (e.g., hexane, heptane, cyclohexane, etc.), ethers (e.g., diethyl ether, diisopropyl ether, tetrahydrofuran, dioxane, etc.), nitriles (e.g., acetonitrile, etc.), ketones (e.g., acetone, etc.), sulfoxides (e.g., dimethylsulfoxide, etc.), acid amides (e.g., N,N-dimethylformamide, etc.), esters (e.g., ethyl acetate, etc.), alcohols (e.g., methanol, ethanol, isopropyl alcohol. etc.), water, and so forth. These solvents may be used singly or in a mixture of two or more kinds at appropriate ratios (e.g., 1:1 to 1:100).

The method of the "crystallization from vapor" includes, for example, a gasification method (sealed tube method, gas stream method), a gas phase reaction method, a chemical transportation method, and so forth.

The method of the "crystallization from a molten form" includes, for example, a normal freezing method (pulling-up method, temperature gradient method, Bridgman method), a zone melting method (zone leveling method, float zone method), a special growth method (VLS method, liquid phase epitaxis method), and so forth.

Examples of the crystal of (R)-lansoprazole or (S)-lansoprazole to be used as a starting material in the crystal production method of the present invention include the following:
(1) a crystal showing an X-ray powder diffraction analysis pattern having characteristic peaks at interplanar spacings (d) of 5.88, 4.70, 4.35, 3.66 and 3.48 Angstrom in an X-ray powder diffraction of wet crystal;
(2) a crystal showing an X-ray powder diffraction analysis pattern having characteristic peaks at interplanar spacings (d) of 8.33, 6.63, 5.86 and 4.82 Angstrom in an X-ray powder diffraction of wet crystal;
(3) a mixture of the crystals of the aforementioned (1) and (2); and
(4) a crystal showing an X-ray powder diffraction analysis pattern having characteristic peaks at interplanar spacings (d) of 11.68, 6.77, 5.84, 5.73, 4.43, 4.09, 3.94, 3.89, 3.69, 3.41 and 3.11 Angstrom.

The enantiomeric excess of (R)-lansoprazole or (S)-lansoprazole to be applied to the crystal production method of the present invention is, for example, not less than about 80% ee, preferably not less than about 90% ee.

More preferable (R)-lansoprazole does not contain (S)-lansoprazole substantially. By "does not contain substantially" is meant (R)-lansoprazole containing (S)-lansoprazole in 0-3%, preferably 0-1%. More preferably, (S)-lansoprazole does not contain (R)-lansoprazole substantially. By "does not contain substantially" here is meant (S)-lansoprazole containing (R)-lansoprazole in 0-3%, preferably 0-1%.

It is preferable that (R)-lansoprazole or (S)-lansoprazole obtained by the above-mentioned production method be subjected to the step to be mentioned below for improving the optical purity.

For an increased optical purity of the (R)-lansoprazole or (S)-lansoprazole obtained by the above-mentioned production method, for example, the method described in JP-A-11-508590 (WO 97/02261) or a method analogous thereto, or the following method [1] or [2] is employed.
[1] A crystal of (R)-lansoprazole is selectively crystallized from a solution containing (R)-lansoprazole in a greater amount than (S)-lansoprazole and the precipitated crystal is separated to give a crystal of (R)-lansoprazole substantially free of (S)-lansoprazole.
[2] A crystal of (S)-lansoprazole is selectively crystallized from a solution containing (S)-lansoprazole in a greater amount than (R)-lansoprazole and the precipitated crystal is separated to give a crystal of (S)-lansoprazole substantially free of (R)-lansoprazole.

It is also possible to separate the precipitated crystal after the above-mentioned [1] or [2] and subject the crystal to recrystallization once or more.

The methods for "selective crystallization" include, for example, a method of stirring a solution, a method of adding a seed crystal to a solution, a method of changing the temperature of a solution, a method of changing the solvent composition of a solution, a method of decreasing the liquid amount of a solution, or a method consisting of two or more of these methods in combination and the like.

The "method of stirring a solution" includes, for example, stirring a solution containing one of (R)-lansoprazole and (S)-lansoprazole in a greater amount than the other at about −80° C. to 120° C., preferably at about −20° C. to 60° C., for about 0.01 to 100 hours, preferably for about 0.1 to 10 hours.

The "method of adding a seed crystal to a solution" include, for example, adding (1) a crystal showing an X-ray powder diffraction analysis pattern having characteristic peaks at interplanar spacings(d) of 5.88, 4.70, 4.35, 3.66 and 3.48 Angstrom; (2) a crystal showing an X-ray powder diffraction analysis pattern having characteristic peaks at interplanar spacings(d) of 8.33, 6.63, 5.86 and 4.82 Angstrom; (3) a mixture of the crystals of the aforementioned (1) and (2) or (4) in a solution, a solid that transforms to the aforementioned (1)-(3) (e.g., a crystal showing an X-ray powder diffraction analysis pattern having characteristic peaks at interplanar spacings(d) of 11.68, 6.77, 5.84, 5.73, 4.43, 4.09, 3.94, 3.89, 3.69, 3.41 and 3.11 Angstrom; a crystal showing an X-ray powder diffraction analysis pattern having characteristic peaks at interplanar spacings(d) of 8.86, 8.01, 6.58, 5.91, 5.63, 5.02 and 4.48 Angstrom; a crystal showing an X-ray powder diffraction analysis pattern having characteristic peaks at interplanar spacings(d) of 8.37, 4.07, 5.65, 5.59, 5.21, 4.81 and 4.21 Angstrom; a crystal showing an X-ray powder diffraction analysis pattern having characteristic peaks at interplanar spacings(d) of 11.68, 6.78, 5.85, 5.73, 4.43, 4.09, 3.94, 3.90, 3.69, 3.41 and 3.11 Angstrom, etc.) to a solution containing one of (R)-lansoprazole and (S)-lansoprazole in a greater amount than the other as a seed crystal.

The "method of changing the temperature of a solution" includes, for example, changing the temperature of a solution containing one of (R)-lansoprazole and (S)-lansoprazole in a greater amount than the other, preferably by cooling (e.g., lower the liquid temperature by 5-100° C.).

The "method of changing the solvent composition of a solution" includes, for example, adding water, a low polar organic solvent (e.g., esters, ethers, aromatic hydrocarbons, hydrocarbons, halogenated hydrocarbons or a mixture of two or more of these etc.) or a mixture of two or more of these to a solution containing one of (R)-lansoprazole and (S)-lansoprazole in a greater amount than the other.

The "method of decreasing the liquid amount of a solution" includes, for example, distilling away or evaporating the solvent from a solution containing one of (R)-lansoprazole and (S)-lansoprazole in a greater amount than the other and the like.

Of these, preferred are:
(i) a method of stirring a solution,
(ii) a method comprising a method of stirring a solution and a method of adding a seed crystal to a solution,
(iii) a method comprising a method of stirring a solution and a method of changing the temperature of a solution,
(iv) a method comprising a method of stirring a solution and a method of changing the solvent composition of a solution,
(v) a method comprising a method of stirring a solution and a method of decreasing the liquid amount of a solution,
(vi) a method comprising a method of stirring a solution, a method of changing the temperature of a solution and a method of adding a seed crystal to a solution,
(vii) a method comprising a method of stirring a solution, a method of changing the solvent composition of a solution and a method of adding a seed crystal to a solution,
(viii) a method comprising a method of stirring a solution, a method of decreasing the liquid amount of a solution and a method of adding a seed crystal to a solution,
(ix) a method comprising a method of stirring a solution, a method of changing the temperature of a solution and a method of changing the solvent composition of a solution,
(x) a method comprising a method of stirring a solution, a method of changing the temperature of a solution, a method of changing the solvent composition of a solution and a method of adding a seed crystal to a solution,
(xi) a method comprising a method of stirring a solution, a method of changing the temperature of a solution and a method of decreasing the liquid amount of a solution, and
(xii) a method comprising a method of stirring a solution, a method of changing the temperature of a solution, a method of decreasing the liquid amount of a solution and a method of adding a seed crystal to a solution.

The precipitated crystal can be separated by, for example, filtration, centrifugation and the like.

The thus-obtained crystal may be used as it is, or dried, where necessary, or may be subjected to a recrystallization step, where necessary.

The "drying" includes, for example, vacuum drying, through-flow drying, drying by heating, air drying and the like.

When, for example, (R)-lansoprazole or (S)-lansoprazole obtained by asymmetric synthesis is used, it is applied to the method of the above-mentioned [1] or [2], or where necessary, recrystallization once or more times to reduce the amount of analogous materials (e.g., 2-[[[3-methyl-4-(2,2,2-trifluoroethoxy)-2-pyridinyl]methyl]thio]-1H-benzimidazole and/or 2-[[[3-methyl-4-(2,2,2-trifluoroethoxy)-2-pyridinyl]methyl]sulfonyl]-1H-benzimidazole, etc.) in the precipitated crystals.

To be specific, the obtained crystal or a dry crystal thereof is dissolved in a solvent (e.g., water, esters, ketones, phenols, alcohols, ethers, aromatic hydrocarbons, amides, sulfoxides, hydrocarbons, nitrites, halogenated hydrocarbons, pyridines or a mixture of two or more of these), applied to a dehydration step where necessary, and crystallized.

The "dehydrating" is performed by a conventional dehydration method, such as a concentration method, a method using a dehydrating agent [e.g., anhydrous magnesium sulfate, anhydrous sodium sulfate, molecular sieve (trade name)] and the like.

Examples of the "crystallization" method include the aforementioned crystallization method.

The crystal obtained after the above-mentioned recrystallization is exemplified by:
(1) a crystal showing an X-ray powder diffraction analysis pattern having characteristic peaks at interplanar spacings (d) of 5.88, 4.70, 4.35, 3.66 and 3.48 Angstrom in an X-ray powder diffraction of wet crystal,
(2) a crystal showing an X-ray powder diffraction analysis pattern having characteristic peaks at interplanar spacings (d) of 8.33, 6.63, 5.86 and 4.82 Angstrom in an X-ray powder diffraction of wet crystal,
(3) a mixture of the crystals of the aforementioned (1) and (2), and
(4) a crystal showing an X-ray powder diffraction analysis pattern having characteristic peaks at interplanar spacings (d) of 11.68, 6.77, 5.84, 5.73, 4.43, 4.09, 3.94, 3.89, 3.69, 3.41 and 3.11 Angstrom.

The amount of the analogous materials in the crystal is less than 1 wt %, preferably less than 0.4 wt %.

The crystal precipitated in the recrystallization step can be separated by, for example, filtration, centrifugation and the like.

The thus-obtained crystal may be used as it is, or dried, where necessary, or may be subjected to a second recrystallization step, where necessary.

The "drying" is done by a method similar to the above-mentioned "drying".

To be specific, the obtained crystal is dissolved in a solvent (e.g., water, esters, ketones, phenols, alcohols, ethers, aromatic hydrocarbons, amides, sulfoxides, hydrocarbons, nitrites, halogenated hydrocarbons, pyridines or a mixture of two or more of these etc.), applied to a dehydration step where necessary, crystallized, separated and dried.

The "dehydrating" is performed by a method such as the above-mentioned "dehydration method".

Examples of the "crystallization" method include the aforementioned crystallization method.

The crystal obtained in the above-mentioned second recrystallization step is exemplified by a crystal of (R)- or (S)-lansoprazole, which shows an X-ray powder diffraction analysis pattern having characteristic peaks at interplanar spacings(d) of 11.68, 6.77, 5.84, 5.73, 4.43, 4.09, 3.94, 3.89, 3.69, 3.41 and 3.11 Angstrom.

The crystal obtained in the second recrystallization step may be separated by, for example, filtration, centrifugation and the like.

The separated crystal can be dried by, for example, vacuum drying, through-flow drying, drying by heating, air drying and the like.

The "esters" include, for example, methyl acetate, ethyl acetate, propyl acetate, isopropyl acetate, butyl acetate, isobutyl acetate, ethyl formate and the like.

The "ketones" include, for example, acetone, methyl ethyl ketone, methyl isopropyl ketone, methyl butyl ketone, methyl isobutyl ketone and the like.

The "phenols" include, for example, anisole and the like.

The "alcohols" include, for example, methanol, ethanol, 1-propanol, 2-propanol, 1-butanol, 2-butanol, 2-methyl-1-propanol, pentanol, 3-methyl-1-butanol, 2-methoxyethanol, 2-ethoxyethanol, ethylene glycol and the like.

The "ethers" include, for example, t-butyl methyl ether, diethyl ether, 1,1-diethoxypropane, 1,1-dimethoxypropane, 2,2-dimethoxypropane, isopropyl ether, tetrahydrofuran, methyltetrahydrofuran and the like.

The "aromatic hydrocarbons" include, for example, chlorobenzene, toluene, xylene, cumene and the like.

The "amides" include, for example, formamide, N,N-dimethylacetamide, N,N-dimethylformamide, N-methylpyrrolidone and the like.

The "sulfoxides" include, for example, dimethylsulfoxide and the like.

The "hydrocarbons" include, for example, propane, hexane, pentane, octane, isooctane and the like.

The "nitriles" include, for example, acetonitrile and the like.

The "halogenated hydrocarbons" include, for example, chloroform, dichloromethane, dichloroethene, trichloroethene and the like.

The "pyridines" include, for example, pyridine and the like.

The crystal obtained by crystallization by the above-mentioned method and dry crystal thereof do not substantially contain the other enantiomer.

(R)-Lansoprazole or (S)-lansoprazole obtained by the above-mentioned various methods is applied to the crystal production method of the present invention.

The crystal production method of the present invention is described in detail in the following.

(1) Step for Crystallization at a Temperature of About 0° C. to About 35° C. from $C_{1-4}$ Alkyl Acetate Solution Containing (R)-lansoprazole or (S)-lansoprazole at a Concentration of About 0.1 g/mL to About 0.5 g/mL First, (R)-lansoprazole or (S)-lansoprazole is made to be present in $C_{1-4}$ alkyl acetate at a concentration of about 0.1 g/mL to about 0.5 g/mL (preferably about 0.1 g/mL to about 0.35 g/mL, more preferably about 0.2 g/mL to about 0.3 g/mL, particularly preferably about 0.25 g/mL to about 0.28 g/mL).

For example, an excess $C_{1-4}$ alkyl acetate is added to (R)-lansoprazole or (S)-lansoprazole, and the mixture is heated where necessary at about 30° C. to 60° C. to dissolve same and concentrated under reduced pressure to achieve a given concentration (about 0.1 g/mL to about 0.5 g/mL).

As used herein, the concentration is measured according to an area comparison method with a standard product solution using high performance liquid chromatography. The measurement method is explained in detail in the following.

Measurement Conditions

Column: Shiseido CAPCELL PAK C18 SG120 5 μm 4.6×250 mm

Column Temp.: 25° C.

Mobile phase: $H_2O:CH_3CN:Et_3N=50:50:1$ (adjusted to pH 7.0 with phosphoric acid)

Flow rate: 1.0 mL/min.

Inject. Vol.: 10 μl

Wavelength: 285 nm

Sample Preparation

Standard solution: standard product (about 75 mg) is precisely weighed and mobile phase is added to make the amount 100 mL.

Sample solution: mobile phase is added to ethyl acetate solution (1 mL) to make the amount 100 mL.

Concentration Measurement Method

Standard solution (10 μl) and sample solution (10 μl) are tested by liquid chromatography under the aforementioned HPLC conditions and peak area $A_S$ of (R)-lansoprazole or (S)-lansoprazole in the Standard solution, and the peak area $A_T$ of (R)-lansoprazole or (S)-lansoprazole in the sample solution are measured by automatic integration, based on which the concentration of (R)-lansoprazole or (S)-lansoprazole is calculated from the following formula:

$(A_T/A_S) \times (W_S/1000)$ $W_S$: standard product sample amount (mg)

The concentration can be made to fall within the optimal range for the selected solvent, wherein the state of saturation or per-saturation (R)-lansoprazole or (S)-lansoprazole is preferable for crystallization.

The $C_{1-4}$ alkyl acetate includes methyl acetate, ethyl acetate, propyl acetate, butyl acetate and the like, of which preferably used are ethyl acetate and propyl acetate.

The crystallization is performed by standing or stirring a $C_{1-4}$ alkyl acetate solution containing the above-mentioned (R)-lansoprazole or (S)-lansoprazole according to a method known per se at a crystallization temperature of about 0° C. to about 35° C.

The lower limit of crystallization temperature is preferably about 10° C., more preferably about 15° C., most preferably about 20° C. The upper limit of crystallization temperature is preferably about 30° C. Particularly, crystallization temperature is preferably about 20° C. to about 30° C.

The crystallization time is about 30 minutes to about 10 hours, preferably about 30 minutes to about 4 hours, particularly preferably about 1 hour to about 2 hours.

In this step, a seed crystal may be added to the solution. Examples of the seed crystal include one that may be added to the solution before or during dropwise addition of $C_{5-8}$ hydrocarbon to be mentioned below.

This step is carried out in an atmosphere or under an inert gas atmosphere, or in an inert gas stream. As the "inert gas", one usable for dropwise addition of $C_{5-8}$ hydrocarbon to be mentioned below is employed.

The crystal obtained by this step can be separated by a method such as filtration, centrifugation and the like.

The separated crystal may be washed, where necessary, with a (1:0-1:10) mixture of $C_{1-4}$ alkyl acetate-$C_{5-8}$ hydrocarbon, and the like. The $C_{1-4}$ alkyl acetate here is exemplified by those mentioned above, and the $C_{5-8}$ hydrocarbon is exemplified by those mentioned below. The separated crystal can be dried by, for example, vacuum drying, through-flow drying, drying by heating, air drying and the like.

The crystal obtained by this step is superior in preservation stability and can be used as the pharmaceutical product to be mentioned below. By the following step (2), the objective crystal superior in preservation stability can be obtained in a high yield.

(2) Step for Adding Dropwise $C_{5-8}$ Hydrocarbon in an Amount of Not More Than 7 Times the Amount of the $C_{1-4}$ Alkyl Acetate Solution at the Same Temperature After Step (1)

By applying this step to the crystal obtained by the above-mentioned step (1) after separation or without separation, the crystal can be obtained in greater amounts.

This step is preferably applied after precipitation of the crystal in the above-mentioned step (1). It is preferably applied after precipitation of a crystal in at least about 20 wt %, more preferably about 30 wt % to about 90 wt %, particularly preferably about 50 wt % to about 90 wt %, of (R)-lansoprazole or (S)-lansoprazole added as a starting material.

The crystallization temperature in this step is the same as in step (1).

Examples of $C_{5-8}$ hydrocarbon include straight chain or branched $C_{5-8}$ aliphatic hydrocarbon, such as pentane, isopentane, neopentane, hexane, isohexane, 3-methylpentane, neohexane, 2,3-dimethylbutane, heptane, 2-methylhexane, 3-methylhexane, 3-ethylpentane, 2,2-dimethylpentane, 2,3-dimethylpentane, 2,4-dimethylpentane, 3,3-dimethylpentane, 2,2,3-trimethylbutane, octane, isooctane and the like, and $C_{7-8}$ aromatic hydrocarbon, such as toluene, xylene and the like. Preferably, heptane and straight chain $C_{5-8}$ aliphatic hydrocarbon such as hexane and the like, are used.

The amount of dropwise addition of $C_{5-8}$ hydrocarbon is not more than 7 times, preferably not more than 5 times, more preferably 1 to 3 times, the amount of the $C_{1-4}$ alkyl acetate solution containing (R)-lansoprazole or (S)-lansoprazole in step (1).

The dropwise addition includes sequential dropwise addition of almost the same amount over, for example, about 15 minutes to about 4 hours (preferably about 1 hour to about 2 hours) while standing or stirring the solution.

The temperature during dropwise addition is preferably adjusted to the above-mentioned crystallization temperature.

In this step, a seed crystal may be added to the solution before or during the dropwise addition of $C_{5-8}$ hydrocarbon.

The seed crystal includes, for example,
(1) a crystal showing an X-ray powder diffraction analysis pattern having characteristic peaks at interplanar spacings (d) of 5.88, 4.70, 4.35, 3.66 and 3.48 Angstrom,
(2) a crystal showing an X-ray powder diffraction analysis pattern having characteristic peaks at interplanar spacings (d) of 8.33, 6.63, 5.86 and 4.82 Angstrom X-ray powder diffraction,
(3) a crystal showing an X-ray powder diffraction analysis pattern having characteristic peaks at interplanar spacings (d) of 11.68, 6.77, 5.84, 5.73, 4.43, 4.09, 3.94, 3.89, 3.69, 3.41 and 3.11 Angstrom,
(4) a crystal showing an X-ray powder diffraction analysis pattern having characteristic peaks at interplanar spacings (d) of 8.86, 8.01, 6.58, 5.91, 5.63, 5.02 and 4.48 Angstrom,
(5) a crystal showing an X-ray powder diffraction analysis pattern having characteristic peaks at interplanar spacings (d) of 8.37, 4.07, 5.65, 5.59, 5.21, 4.81 and 4.21 Angstrom,
(6) a crystal showing an X-ray powder diffraction analysis pattern having characteristic peaks at interplanar spacings (d) of 11.68, 6.78, 5.85, 5.73, 4.43, 4.09, 3.94, 3.90, 3.69, 3.41 and 3.11 Angstrom,
(7) a mixture of two or more crystals from the aforementioned (1)-(6) and
(8) a solid that transforms into the aforementioned (1)-(6) in a solution.

After the dropwise addition, the mixture may be stood or stirred on demand for about 1 hour to about 3 hours.

This step is applied in an atmosphere or under an inert gas atmosphere, or in an inert gas stream. The "inert gas" includes, for example, nitrogen, helium, neon, argon and the like.

The crystal obtained by this step can be separated by filtration, centrifugation and the like.

The separated crystal may be washed, where necessary, with a $C_{1-4}$ alkyl acetate —$C_{5-8}$ hydrocarbon (1:0-1:10) mixture and the like. As used herein, the $C_{1-4}$ alkyl acetate and $C_{5-8}$ hydrocarbon are exemplified by those mentioned above. The separated crystal can be dried by, for example, vacuum drying, through-flow drying, drying by heating, air drying and the like.

The obtained crystal can be analyzed generally by crystal analysis by X-ray diffraction. The orientation of the crystal can be determined by a mechanical method, optical method and the like.

The crystal obtained by the above-mentioned production method (step (1) alone, or step (2) after step (1)) has the following melting start temperature by DSC measurement (temperature rise rate 0.5° C./min). As used herein, the "melting start temperature" refers to the temperature at which crystals start to melt when heated under, for example, the DSC measurement conditions to be mentioned below. The crystal has the melting start temperature of not less than about 131° C., preferably about 131° C. to about 137° C., more preferably about 132° C. to about 135° C., most preferably about 133° C. to about 135° C., particularly preferably about 135° C. For example, the melting start temperature of the crystal obtained in the above-mentioned step (1) can be about 135° C. In addition, the melting start temperature of the crystal obtained by step (2) after applying the above-mentioned step (1) can be about 132° C. to about 135° C.

The melting start temperature of the crystal obtained by a conventional method is less than about 131° C. For example, the melting start temperature of the crystal obtained by the method of Reference Example 3 mentioned below was about 125° C. to about 130° C.

The crystal having a melting start temperature of not less than about 131° C., which is obtained by the production method of the present invention, has extremely superior preservation stability as compared to the crystal having a melting start temperature of less than about 131° C., which is obtained by a prior art method. In the stability test (40° C.—one month residual ratio, 60° C.—one month residual ratio) to be mentioned below, for example, the crystal obtained by the production method of the present invention showed a residual ratio of not less than 99%, but the ratio of the crystal obtained by a conventional method was less than 94%. Moreover, the crystal obtained by a conventional method showed noticeable coloring during preservation.

The crystal having a melting start temperature of not less than about 131° C., which is obtained by the production method of the present invention, has such superior preservation stability and can be used advantageously as a pharmaceutical product, as compared to the crystal having a melting start temperature of less than about 131° C., which is obtained by a prior art method.

The crystal of (R)-lansoprazole or (S)-lansoprazole obtained by the crystal production method of the present invention is useful as a pharmaceutical product because it shows excellent antiulcer activity, gastric acid secretion-inhibiting action, mucosa-protecting action, anti-*Helicobacter pylori* action, etc., and because it is of low toxicity. The dry crystal of (R)-lansoprazole or (S)-lansoprazole is stabler than a precipitated crystal (wet crystal) of (R)-lansoprazole or (S)-lansoprazole, and when it is used as a pharmaceutical product, a dry crystal of (R)-lansoprazole or (S)-lansoprazole is preferably used.

The crystal or dry crystal obtained by the method of the present invention is useful for mammals (e.g., humans, monkeys, sheep, bovines, horses, dogs, cats, rabbits, rats, mice, etc.) in the treatment and prevention of digestive ulcer (e.g., gastric ulcer, duodenal ulcer, stomach ulcer, Zollinger-Ellison syndrome, etc.), gastritis, reflux esophagitis, NUD (non-ulcer dyspepsia), gastric cancer (inclusive of gastric cancer caused by promotion of interleukin-1β production due to genetic polymorphism of interleukin-1) and gastric MALT lymphoma; *Helicobacter pylori* eradication; suppression of upper gastrointestinal hemorrhage due to digestive ulcer, acute stress ulcer and hemorrhagic gastritis; suppression of upper gastrointestinal hemorrhage due to invasive stress (stress from major surgery necessitating intensive management after surgery, and from cerebral vascular disorder, head trauma, multiple organ failure and extensive burn necessitating intensive treatment); treatment and prevention of ulcer caused by a nonsteroidal anti-inflammatory agent; treatment and prevention of hyperacidity and ulcer due to postoperative stress; pre-anesthetic administration and the like. For eradication of *Helicobacter pylori*, the crystal or dry crystal obtained by the method of the present invention and antibiotic penicillins (e.g., amoxicillin etc.) and antibiotic erythromycins (e.g., clarithromycin, etc.) are preferably used.

For the above-mentioned various pharmaceutical uses, the crystal of (R)-lansoprazole is preferably used.

The crystal of the present invention can be safely administered orally or non-orally (e.g., topical, rectal and intravenous administration, etc.), as such or in the form of pharmaceutical compositions formulated with a pharmacologically acceptable carrier, e.g., tablets (including sugar-coated tablets and film-coated tablets), powders, granules, capsules (including soft capsules), orally disintegrating tablets, liquids, injectable preparations, suppositories, sustained-release preparations and patches, in accordance with a commonly known method.

The content of the crystal of the present invention in the pharmaceutical composition of the present invention is about 0.01 to 100 wt % relative to the entire composition. Varying depending on subject of administration, route of administration, target disease etc., its dose is normally about 0.5 to 1,500 mg/day, preferably about 5 to 150 mg/day, based on the active ingredient, when, for example, it is orally administered as an antiulcer agent to an adult human (60 kg). The crystal of the present invention may be administered once daily or in 2 to 3 divided portions per day.

Pharmacologically acceptable carriers that may be used to produce the pharmaceutical composition of the present invention include various organic or inorganic carrier substances in common use as pharmaceutical materials, including excipients, lubricants, binders, disintegrants, water-soluble polymers and basic inorganic salts for solid preparations; and solvents, dissolution aids, suspending agents, isotonicity agents, buffers and soothing agents for liquid preparations. Other ordinary pharmaceutical additives such as preservatives, antioxidants, coloring agents, sweetening agents, souring agents, bubbling agents and flavorings may also be used as necessary.

Such "excipients" include, for example, lactose, sucrose, D-mannitol, starch, cornstarch, crystalline cellulose, light silicic anhydride, titanium oxide and the like.

Such "lubricants" include, for example, magnesium stearate, sucrose fatty acid esters, polyethylene glycol, talc, stearic acid and the like.

Such "binders" include, for example, hydroxypropyl cellulose, hydroxypropylmethyl cellulose, crystalline cellulose, α-starch, polyvinylpyrrolidone, gum arabic powder, gelatin, pullulan, low-substituted hydroxypropyl cellulose and the like.

Such "disintegrants" include (1) crosslinked povidone, (2) what is called super-disintegrants such as crosslinked carmellose sodium (FMC-Asahi Chemical) and carmellose calcium (Gotoku Yakuhin), (3) carboxymethyl starch sodium (e.g., product of Matsutani Chemical), (4) low-substituted hydroxypropyl cellulose (e.g., product of Shin-Etsu Chemical), (5) cornstarch, and so forth. Said "crosslinked povidone" may be any crosslinked polymer having the chemical name 1-ethenyl-2-pyrrolidinone homopolymer, including, what is called, polyvinylpyrrolidone (PVPP) and 1-vinyl-2-pyrrolidinone homopolymer, and is exemplified by Colidon CL (produced by BASF), Polyplasdon XL (produced by ISP), Polyplasdon XL-10 (produced by ISP), Polyplasdon INF-10 (produced by ISP) and the like.

Such "water-soluble polymers" include, for example, ethanol-soluble water-soluble polymers [e.g., cellulose derivatives such as hydroxypropyl cellulose (hereinafter also referred to as HPC), polyvinylpyrrolidone etc.], ethanol-insoluble water-soluble polymers [e.g., cellulose derivatives such as hydroxypropylmethyl cellulose (hereinafter also referred to as HPMC), methyl cellulose and carboxymethyl cellulose sodium, sodium polyacrylate, polyvinyl alcohol, sodium alginate, guar gum etc.] and the like.

Such "basic inorganic salts" include, for example, basic inorganic salts of sodium, potassium, magnesium and/or calcium. Preferred are basic inorganic salts of magnesium and/or calcium. More preferred are basic inorganic salts of magnesium. Such basic inorganic salts of sodium include, for example, sodium carbonate, sodium hydrogen carbonate, disodium hydrogenphosphate, etc. Such basic inorganic salts of potassium include, for example, potassium carbonate, potassium hydrogen carbonate, etc. Such basic inorganic salts of magnesium include, for example, heavy magnesium carbonate, magnesium carbonate, magnesium oxide, magnesium hydroxide, magnesium metasilicate aluminate, magnesium silicate, magnesium aluminate, synthetic hydrotalcite [$Mg_6Al_2(OH)_{16}.CO_3.4H_2O$], alumina hydroxide magnesium, and so forth. Among others, preferred is heavy magnesium carbonate, magnesium carbonate, magnesium oxide, magnesium hydroxide, etc. Such basic inorganic salts of calcium include, for example, precipitated calcium carbonate, calcium hydroxide and the like.

Such "solvents" include, for example, water for injection, alcohol, propylene glycol, macrogol, sesame oil, corn oil, olive oil and the like.

Such "dissolution aids" include, for example, polyethylene glycol, propylene glycol, D-mannitol, benzyl benzoate, ethanol, trisaminomethane, cholesterol, triethanolamine, sodium carbonate, sodium citrate and the like.

Such "suspending agents" include, for example, surfactants such as stearyltriethanolamine, sodium lauryl sulfate, laurylaminopropionic acid, lecithin, benzalkonium chloride, benzethonium chloride and monostearic glycerol; and hydrophilic polymers such as polyvinyl alcohol, polyvinylpyrrolidone, carboxymethyl cellulose sodium, methyl cellulose, hydroxymethyl cellulose, hydroxyethyl cellulose and hydroxypropyl cellulose.

Such "isotonicity agents" include, for example, glucose, D-sorbitol, sodium chloride, glycerol, D-mannitol and the like.

Such "buffers" include, for example, buffer solutions of phosphates, acetates, carbonates, citrates and the like.

Such "soothing agents" include, for example, benzyl alcohol and the like.

Such "preservatives" include, for example, p-oxybenzoic acid esters, chlorobutanol, benzyl alcohol, phenethyl alcohol, dehydroacetic acid, sorbic acid and the like.

Such "antioxidants" include, for example, sulfites, ascorbic acid, α-tocopherol and the like.

Such "coloring agents" include, for example, foodcolors such as Food Color Yellow No. 5, Food Color Red No. 2 and Food Color Blue No. 2; and food lake colors, Bengal and the like.

Such "sweetening agents" include, for example, saccharin sodium, dipotassium glycyrrhetinate, aspartame, stevia, thaumatin and the like.

Such "souring agents" include, for example, citric acid (citric anhydride), tartaric acid, malic acid and the like.

Such "bubbling agents" include, for example, sodium bicarbonate and the like.

Such "flavorings" may be synthetic substances or naturally occurring substances, and include, for example, lemon, lime, orange, menthol, strawberry and the like.

The crystal of the present invention may be prepared as a preparation for oral administration in accordance with a commonly known method, by, for example, compressionshaping it in the presence of an excipient, a disintegrant, a binder, a lubricant or the like, and subsequently coating it as necessary by a commonly known method for the purpose of taste masking, enteric dissolution or sustained release. For an enteric preparation, an intermediate layer may be provided by a commonly known method between the enteric layer and the drug-containing layer for the purpose of separation of the two layers.

For preparing the crystal of the present invention as an orally disintegrating tablet, available method include, for example, a method in which a core containing crystalline cellulose and lactose is coated with the crystal of the present invention and a basic inorganic salt, and is further coated with a coating layer containing a water-soluble polymer, to give a composition, which is coated with an enteric coating layer containing polyethylene glycol, further coated with an enteric coating layer containing triethyl citrate, still further coated with an enteric coating layer containing polyethylene glycol, and still yet further coated with mannitol, to give fine granules, which are mixed with additives and shaped. The above-mentioned "enteric coating layer" includes, for example, aqueous enteric polymer substrates such as cellulose acetate phthalate (CAP), hydroxypropylmethyl cellulose phthalate, hydroxymethyl cellulose acetate succinate, methacrylic acid copolymers [e.g., Eudragit L30D-55 (trade name; produced by Rohm), Colicoat MAE30DP (trade name; produced by BASF), Polykid PA30 (trade name; produced by San-yo Chemical) etc.], carboxymethylethyl cellulose and shellac; sustained-release substrates such as methacrylic acid polymers [e.g., Eudragit NE30D (trade name), Eudragit RL30D (trade name), Eudragit RS30D (trade name), etc.]; water-soluble polymers; plasticizers such as triethyl citrate, polyethylene glycol, acetylated monoglycerides, triacetine and castor oil; and mixtures of one or more thereof. The above-mentioned "additive" includes, for example, water-soluble sugar alcohols (e.g., sorbitol, mannitol, multitol, reduced starch saccharides, xylitol, reduced paratinose, erythritol. etc.), crystalline cellulose [e.g. Ceolas KG 801, Avicel PH 101, Avicel PH 102, Avicel PH 301, Avicel PH 302, Avicel RC-591 (crystalline cellulose carmellose sodium) etc.], low-substituted hydroxypropyl cellulose [e.g., LH-22, LH-32, LH-23, LH-33 (Shin-Etsu Chemical) and mixtures thereof etc.] etc.; binders, souring agents, bubbling agents, sweetening agents, flavorings, lubricants, coloring agents, stabilizers, excipients, disintegrants etc. are also used.

The crystal of the present invention may be used in combination with 1 to 3 other active ingredients.

Such "other active ingredients" include, for example, anti-*Helicobacter pylori* activity substances, imidazole compounds, bismuth salts, quinolone compounds, and so forth. Of these substances, preferred are anti-*Helicobacter pylori* action substances, imidazole compounds etc. Such "anti-*Helicobacter pylori* action substances" include, for example, antibiotic penicillins (e.g., amoxicillin, benzylpenicillin, piperacillin, mecillinam, etc.), antibiotic cefems (e.g., cefixime, cefaclor, etc.), antibiotic macrolides (e.g., erythromycin, clarithromycin, etc.), antibiotic tetracyclines (e.g., tetracycline, minocycline, streptomycin. etc.), antibiotic aminoglycosides (e.g., gentamicin, amikacin, etc.), imipenem, and so forth. Of these substances, preferred are antibiotic penicillins, antibiotic macrolides etc. Especially preferred is a triple therapy of an antibiotic penicillins, anantibiotic macrolide and the crystal of (R)-lansoprazole or (S)-lansoprazole. Such "imidazole compounds" include, for example, metronidazole, miconazole, etc. Such "bismuth salts" include, for example, bismuth acetate, bismuth citrate, etc. Such "quinolone compounds" include, for example, ofloxacin, ciploxacin, etc.

Such "other active ingredients" and the crystal of the present invention may also be used in combination as a mixture prepared as a single pharmaceutical composition [e.g., tablets. powders, granules, capsules (including soft capsules), liquids, injectable preparations, suppositories, sustained-release preparations, etc.], in accordance with a commonly known method. and may also be prepared as separate preparations and administered to the same subject simultaneously or at a time interval.

While the present invention is explained in detail in the following by referring to Reference Examples and Examples, the present invention is not limited by these Examples.

The X-ray powder diffraction was measured using X-ray Diffractometer RINT Ultima+ (Rigaku).

The melting start temperature was measured using DSC (differential scanning calorimeter SEIKO DSC220C) under the following measurement conditions.

DSC Measurement Conditions;
temperature range: room temperature to 220° C.
temperature rise rate: 0.5° C./min.
sample container: aluminum pan (without cover)
atmosphere: nitrogen gas (100 mL/min)

Enantiomeric excess (% ee) was measured by high performance liquid chromatography using an optically active column for the following conditions (A).

The amounts of sulfide and sulfone present were measured by high performance liquid chromatography using an optically active column for the following conditions (A) or high performance liquid chromatography under the conditions (B).

High Performance Liquid Chromatography Conditions (A);
Column: CHIRALCEL OD (4.6×250 mm; DAICEL CHEMICAL INDUSTRIES, LTD.)
Mobile phase: hexane/ethanol=90/10
Flow rate: 1.0 mL/min
Detection: UV 285 nm High Performance Liquid Chromatography Conditions (B);
Column: CAPCELL PAK C18 SG120 5 μm 4.6×250 mm (Shiseido Co., Ltd.)
Mobile Phase: acetonitrile:water:triethylamine mixture (50:50:1) adjusted to pH 7.0 with phosphoric acid
Flow rate: 1.0 mL/min
Detection: UV 285 nm Reference Example 1

Production of Solution Containing (R)-2-[[[3-methyl-4-(2,2,2-trifluoroethoxy)-2-pyridinyl]methyl]sulfinyl]-1H-benzimidazole by Asymmetric Oxidation 2-[[[3-Methyl-4-(2,2,2-trifluoroethoxy)-2-pyridinyl]methyl]thio]-1H-benzimidazole monohydrate (6 kg, 16.2 mol) was dried in vacuo at 80° C. for 21 hours to give 2-[[[3-methyl-4-(2,2,2-trifluoroethoxy)-2-pyridinyl]methyl]thio]-1H-benzimidazole (5.73 kg, water content 0.0364%). 2-[[[3-Methyl-4-(2,2,2-trifluoroethoxy)-2-pyridinyl]methyl]thio]-1H-benzimidazole (5.00 kg, 14.1 mol, containing water 1.82 g), toluene (25 L), water (13.18 g, 0.732 mol, as total water content 0.833 mol) and (+)-diethyl tartrate (531 mL, 3.10 mol) were mixed under a nitrogen gas stream. Titanium(IV) isopropoxide (414 mL, 1.40 mol) was added at 50-60° C. under a nitrogen gas stream, and the mixture was stirred at the same temperature for 30 min. Diisopropylethylamine (815 mL, 4.68 mol) was added under a nitrogen gas stream at 15-25° C., and cumene hydroperoxide (7.65 L, content 82%, 42.7 mol) was added at −10° C. to 5° C. and the mixture was stirred at −8° C. to 2° C. for 3 hours to allow reaction.

The analysis results of the reaction mixture by high performance liquid chromatography (conditions (A)) are as follows.

The enantiomeric excess of (R)-2-[[[3-methyl-4-(2,2,2-trifluoroethoxy)-2-pyridinyl]methyl]sulfinyl]-1H-benzimidazole in the reaction mixture was 96.9% ee.

As a result of the analysis of the reaction mixture by high performance liquid chromatography (conditions (B)), analogous materials in the reaction mixture were found to be sulfide 1.0% and sulfone 1.7% alone.

Reference Example 2

Purification Method of (R)-2-[[[3-methyl-4-(2,2,2-trifluoroethoxy)-2-pyridinyl]methyl]sulfinyl]-1H-benzimidazole (1) To the reaction mixture obtained in the above-mentioned Reference Example 1 was added 30% aqueous sodium thiosulfate solution (13.5 kg) under a nitrogen gas stream, and the remaining cumene hydroperoxide was decomposed. The mixture was concentrated under reduced pressure until the liquid amount became about 25 L. Heptane-t-butyl methyl ether (heptane:t-butyl methyl ether=1:1, 20 L) was added dropwise while maintaining the mixture at 0-10° C. and heptane (70 L) was added dropwise. The precipitated crystals were separated, and washed with cooled t-butyl methyl ether-toluene (t-butyl methyl ether:toluene=4:1, 5 L).

As a result of the analysis of the crystal by high performance liquid chromatography (conditions (A)), the enantiomeric excess of (R)-2-[[[3-methyl-4-(2,2,2-trifluoroethoxy)-2-pyridinyl]methyl]sulfinyl]-1H-benzimidazole in the crystal was found to be 98.3% ee.

As a result of the analysis of the reaction mixture by high performance liquid chromatography (conditions (B)), analogous materials in the reaction mixture were found to be sulfide 0.45% and sulfone 1.8% alone.

(2) A suspension of the wet crystal obtained in the above-mentioned (1) in acetone (20 L) was added dropwise to a mixture of acetone (7.5 L) and water (37.5 L), and water (52.5 L) was added. The precipitated crystals were separated and washed with cooled acetone-water (acetone:water=1:3, 5 L) and water (6.5 L).

As a result of the analysis of the crystal by high performance liquid chromatography (conditions (A)), the enantiomeric excess of (R)-2-[[[3-methyl-4-(2,2,2-trifluoroethoxy)-2-pyridinyl]methyl]sulfinyl]-1H-benzimidazole in the crystal was found to be 100% ee.

As a result of the analysis of the crystal by high performance liquid chromatography (conditions (B)), analogous materials in the crystal were found to be sulfide 0.19% and sulfone 0.08% alone.

(3) The wet crystal obtained in the above-mentioned (2) was suspended in ethyl acetate (50 L) and magnesium sulfate (2.5 kg) was added. Magnesium sulfate was separated and the residue was washed with ethyl acetate (3.5 L). After addition of triethylamine (250 mL), the mixture was concentrated under reduced pressure until the liquid amount became about 10 L. To the concentrate were added methanol (2.5 L), about 12.5% aqueous ammonia (25.5 L, about 50° C.) and t-butyl methyl ether (24.5 L, about 50° C.) for partitioning. About 12.5% aqueous ammonia (12 L, about 50° C.) was added to the organic layer and the mixture was partitioned (this step was repeated once). The aqueous layers were combined, ethyl acetate (24.5 L) was added, and acetic acid was added dropwise at not more than 20° C. to adjust the pH to about 8. After partitioning, the aqueous layer was extracted with ethyl acetate (24.5 L). The organic layers were combined and washed with about 20% brine (24.5 L). After addition of triethylamine (250 mL), the organic layer was concentrated under reduced pressure. Acetone (5.55 L) was added to the concentrate and the mixture was concentrated under reduced pressure. The concentrate was dissolved in acetone (10 L) and the solution was added dropwise to a mixture of acetone (5 L) and water (25 L). Water (20 L) was added dropwise to the obtained mixture. The precipitated crystal was separated and successively washed with cooled acetone-water (1:3, 4 L) and water (13 L).

As a result of the analysis of the crystal by high performance liquid chromatography (conditions (A)), the enantiomeric excess of (R)-2-[[[3-methyl-4-(2,2,2-trifluoroethoxy)-2-pyridinyl]methyl]sulfinyl]-1H-benzimidazole in the crystal was found to be 100% ee.

As a result of the analysis of the crystal by high performance liquid chromatography (conditions (B)), analogous materials in the crystal were found to be sulfide 0.018% and sulfone 0.016% alone.

Reference Example 3

Purification Method of (R)-2-[[[3-methyl-4-(2,2,2-trifluoroethoxy)-2-pyridinyl]methyl]sulfinyl]-1H-benzimidazole The wet crystal obtained by the method of the above-mentioned Reference Example 2 was dissolved in ethyl acetate (43 L). The separated aqueous layer was partitioned and the obtained organic layer was concentrated under reduced pressure until the liquid amount became about 19 L. Ethyl acetate (48 L) was added to the concentrate, and the mixture was concentrated under reduced pressure until the liquid amount became about 19 L. Ethyl acetate (48 L) and activated carbon (360 g) were added to the concentrate and the mixture was stirred and the activated carbon was filtered off. The filtrate was concentrated under reduced pressure until the liquid amount became about 19 L. Heptane (150 L) was added dropwise to the concentrate at about 40° C. The mixture was stirred at the same temperature for about 30 minutes and the crystal was separated and washed with ethyl acetate-heptane (1:8, 8 L, about 40° C.) and dried to give the title compound (4.5 kg).

The analysis results of the crystal by X-ray powder diffraction are as follows.

The crystal showed an X-ray powder diffraction analysis pattern having characteristic peaks at interplanar spacings(d) of 11.68, 6.77, 5.84, 5.73, 4.43, 4.09, 3.94, 3.89, 3.69, 3.41 and 3.11 Angstrom.

As a result of the analysis of the crystal by high performance liquid chromatography (conditions (A)), analogous materials in the crystal were found to be sulfone 0.02% alone, and other analogous materials such as sulfide and the like were not found. The enantiomeric excess of (R)-lansoprazole in the crystal was 100% ee.

The melting start temperature of the crystal was 127.5° C.

Reference Example 4

Production of (S)-lansoprazole (1) 2-[[[3-Methyl-4-(2,2,2-trifluoroethoxy)-2-pyridinyl]methyl]thio]-1H-benzimidazole (50.0 g, 0.14 mol, containing water 20 mg), toluene (250 mL), water (130 mg, 0.0072 mol, total water content 0.0083 mol) and (−)-diethyl tartrate (5.31 mL, 0.031 mol) were mixed under a nitrogen atmosphere. Titanium(IV) isopropoxide (4.14 mL, 0.014 mol) was added to the mixture at 50° C. and the mixture was stirred at 50-55° C. for 1 hour under a nitrogen atmosphere. Diisopropylethylamine (8.13 mL, 0.047 mol) was added to the obtained mixture under a nitrogen atmosphere and cooling, and cumene hydroperoxide (76.50 mL, content 82%, 0.42 mol) was added at −10° C. to 0° C. The mixture was stirred at −5° C. to 5° C. for 3.5 hours to give a reaction mixture.

As a result of the analysis of the reaction mixture by high performance liquid chromatography (conditions (A)), the enantiomeric excess of (S)-lansoprazole in the reaction mixture was 96.5% ee.

As a result of the analysis of the reaction mixture by high performance liquid chromatography (conditions (B)), analogous materials in the reaction mixture were found to be sulfone 1.90% and sulfide 1.50% alone.

(2) To the reaction mixture obtained in the above-mentioned (1) was added 30% aqueous sodium thiosulfate solution (180 mL) under a nitrogen gas stream, and the remaining cumene hydroperoxide was decomposed. The mixture was partitioned, and water (50 mL), heptane (150 mL), t-butyl methyl ether (200 mL) and heptane (300 mL) were successively added to the obtained organic layer to allow crystallization. The crystal was separated and washed with t-butyl methyl ether-toluene (t-butyl methyl ether: toluene=4:1, 45 mL) to give (S)-lansoprazole having interplanar spacings(d) in the following X-ray powder diffraction, as a wet crystal.

As a result of the analysis of the crystal by X-ray powder diffraction, the wet crystal showed an X-ray powder diffraction analysis pattern having characteristic peaks at interplanar spacings(d) of 5.88, 4.70, 4.35, 3.66 and 3.48 Angstrom.

As a result of the analysis of the crystal by high performance liquid chromatography (conditions (A)), the enantiomeric excess of the crystal was 100% ee.

As a result of the analysis of the crystal by high performance liquid chromatography (conditions (B)), the analogous material in the crystal was sulfone 0.72% and other analogous materials such as sulfide and the like were not found.

(3) A suspension of the wet crystal obtained in the above-mentioned (2) in acetone (220 mL) was added dropwise to a mixture of acetone (75 mL) and water (370 mL), and then water (520 mL) was added. The precipitated crystal was separated and washed with acetone-water (acetone: water=1:3, 44 mL) and water (130 mL) to give a wet crystal of (S)-lansoprazole having interplanar spacings(d) in the following X-ray powder diffraction.

As a result of the analysis of the wet crystal by X-ray powder diffraction, the crystal showed an X-ray powder diffraction analysis pattern having characteristic peaks at interplanar spacings(d) of 8.33, 6.63, 5.86 and 4.82 Angstrom.

As a result of the analysis of the crystal by high performance liquid chromatography (conditions (A)), the enantiomeric excess of the crystal was 100% ee.

As a result of the analysis of the crystal by high performance liquid chromatography (conditions (B)), analogous materials such as sulfone, sulfide and the like were not found.

Reference Example 5

Production of (S)-lansoprazole

The wet crystal (containing the title compound 35.37 g, content of analogous materials: 0%, enantiomeric excess: 100% ee) obtained according to Reference Example 4 was dissolved in ethyl acetate (340 mL). The aqueous layer was separated by partitioning and the obtained organic layer was concentrated under reduced pressure until the liquid amount became about 100 mL. Ethyl acetate (400 mL) and activated carbon (3 g) were added to the concentrate and the mixture was stirred. The activated carbon was removed by filtration. The filtrate was concentrated under reduced pressure until the liquid amount became about 100 mL. Heptane (1000 mL) was added dropwise to the concentrate at about 40° C. The mixture was stirred at the same temperature for about 30 minutes, and the crystal was separated and washed with ethyl acetate-heptane (1:8, 63 mL, about 40° C.). The crystal was dried to give the title compound (35.08 g, yield: 99.2%).

As a result of the analysis of the crystal by X-ray powder diffraction, the crystal showed an X-ray powder diffraction analysis pattern having characteristic peaks at interplanar spacings(d) of 11.68, 6.77, 5.84, 5.73, 4.43, 4.09, 3.94, 3.89, 3.69, 3.41 and 3.11 Angstrom.

As a result of the analysis of the crystal by high performance liquid chromatography (conditions (A)), analogous materials such as sulfone, sulfide and the like were not found in the crystal. The enantiomeric excess of (S)-lansoprazole in the crystal was 100% ee.

The melting start temperature of the crystal was 127.0° C.

Reference Example 6

The crystal (1.5 g, 4.06 mmol) of (R)-2-[[[3-methyl-4-(2,2,2-trifluoroethoxy)-2-pyridinyl]methyl]sulfinyl]-1H-benzimidazole was dissolved in ethyl acetate (30 mL) and concentrated to 6 mL under reduced pressure at an outer temperature of about 25° C. Heptane (24 mL) was added dropwise at about −5° C. for about 30 minutes. After stirring for about 2.5 hours, the precipitated crystal was separated and dried to give the title compound (1.46 g, yield: 97.3%).

As a result of the analysis of the crystal by X-ray powder diffraction, the crystal showed an X-ray powder diffraction analysis pattern having characteristic peaks at interplanar spacings(d) of 11.68, 6.77, 5.84, 5.73, 4.43, 4.09, 3.94, 3.89, 3.69, 3.41 and 3.11 Angstrom.

As a result of the analysis of the crystal by high performance liquid chromatography (conditions (A)), analogous materials such as sulfone, sulfide and the like were not found in the crystal. The enantiomeric excess of (R)-lansoprazole in the crystal was 100% ee.

The melting start temperature of the crystal was 130.0° C.

Reference Example 7

The crystal (1.5 g, 4.06 mmol) of (R)-2-[[[3-methyl-4-(2,2,2-trifluoroethoxy)-2-pyridinyl]methyl]sulfinyl]-1H-benzimidazole was dissolved in ethyl acetate (30 mL) and concentrated to 20 mL under reduced pressure at an outer temperature of about 25° C. Heptane (90 mL) was added dropwise at about 25° C. for about 30 minutes. After stirring for about 2.5 hours, the precipitated crystal was separated and dried to give the title compound (1.40 g, yield: 93.3%).

As a result of the analysis of the crystal by X-ray powder diffraction, the crystal showed an X-ray powder diffraction analysis pattern having characteristic peaks at interplanar spacings(d) of 11.68, 6.77, 5.84, 5.73, 4.43, 4.09, 3.94, 3.89, 3.69, 3.41 and 3.11 Angstrom.

As a result of the analysis of the crystal by high performance liquid chromatography (conditions (A)), analogous materials such as sulfone, sulfide and the like were not found in the crystal. The enantiomeric excess of (R)-lansoprazole in the crystal was 100% ee.

The melting start temperature of the crystal was 128.5° C.

EXAMPLE 1

Production Method of High Melting Point Crystal of (R)-2-[[[3-methyl-4-(2,2,2-trifluoroethoxy)-2-pyridinyl]methyl]sulfinyl]-1H-benzimidazole The wet crystal obtained according to the method of the above-mentioned Reference Example 2 was dissolved in ethyl acetate (50 L). The mixture was partitioned and the organic layer was concentrated under reduced pressure until the liquid amount became about 25 L. Ethyl acetate (30 L) was added to the concentrate, and the mixture was concentrated under reduced pressure until the liquid amount became about 15 L. Ethyl acetate (30 L) and activated carbon (150 g) were added to the concentrate. The activated carbon was removed and the mixture was washed with ethyl acetate (1.5 L). The filtrate was concentrated under reduced pressure until the concentration of (R)-2-[[[3-methyl-4-(2,2,2-trifluoroethoxy)-2-pyridinyl]methyl]sulfinyl]-1H-benzimidazole became about 0.28 g/mL (12.5 L). The mixture was stirred under a nitrogen gas stream, at about 25° C. for about 2 hours, and after confirmation of crystal precipitation, heptane (25 L) was dropwise added over about 1.5 hours, and the mixture was stirred for about 1.5 hours. The precipitated crystal was separated, washed with ethyl acetate-heptane (ethyl acetate:heptane=1:5, 6 L) and dried to give the title compound (3.66 kg, yield: 70% based on 2-[[[3-methyl-4-(2,2,2-trifluoroethoxy)-2-pyridinyl]methyl]thio]-1H-benzimidazole).

As a result of the analysis of the crystal by X-ray powder diffraction, the crystal showed an X-ray powder diffraction analysis pattern having characteristic peaks at interplanar spacings(d) of 11.68, 6.77, 5.84, 5.73, 4.43, 4.09, 3.94, 3.89, 3.69, 3.41 and 3.11 Angstrom.

As a result of the analysis of the crystal by high performance liquid chromatography (conditions (A)), the enantiomeric excess of (R)-2-[[[3-methyl-4-(2,2,2-trifluoroethoxy)-2-pyridinyl]methyl]sulfinyl]-1H-benzimidazole in the crystal was 100% ee.

As a result of the analysis of the crystal by high performance liquid chromatography (conditions (B)), the analogous material was sulfone 0.01% alone, and sulfide and the like were not found. The melting start temperature of the crystal was 134.0° C.

EXAMPLE 2

The crystal (3 g, 8.12 mmol) of (R)-2-[[[3-methyl-4-(2,2,2-trifluoroethoxy)-2-pyridinyl]methyl]sulfinyl]-1H-benzimidazole was dissolved in ethyl acetate (12 mL) at about 50° C. and the solution was stirred at about 25° C. for about 6 hours. The precipitated crystal was separated, washed with ethyl acetate-heptane (ethyl acetate:heptane=1:5, 3 mL) and dried to give the title compound (1.55 g, yield: 52%).

As a result of the analysis of the crystal by X-ray powder diffraction, the crystal showed an X-ray powder diffraction analysis pattern having characteristic peaks at interplanar spacings(d) of 11.68, 6.77, 5.84, 5.73, 4.43, 4.09, 3.94, 3.89, 3.69, 3.41 and 3.11 Angstrom.

As a result of the analysis of the crystal by high performance liquid chromatography (conditions (A)), analogous materials such as sulfone, sulfide and the like were not found. The enantiomeric excess of (R)-lansoprazole in the crystal was 100% ee.

The melting start temperature of the crystal was 135.0° C.

EXAMPLE 3

The crystal (1.5 g, 4.06 mmol) of (R)-2-[[[3-methyl-4-(2,2,2-trifluoroethoxy)-2-pyridinyl]methyl]sulfinyl]-1H-benzimidazole was dissolved in n-propyl acetate (30 mL) and concentrated to 6 mL under reduced pressure at an outer temperature of about 25° C. After stirring for about 2.5 hours, the precipitated crystal was separated and dried to give the title compound (0.94 g, yield: 63%).

The melting start temperature of the crystal was 134.5° C.

EXAMPLE 4

The crystal (3.0 g, 8.12 mmol) of (R)-2-[[[3-methyl-4-(2,2,2-trifluoroethoxy)-2-pyridinyl]methyl]sulfinyl]-1H-benzimidazole was dissolved in ethyl acetate (12 mL) at about 50° C. The mixture was stirred at about 25° C. for about 2.5 hours, and after confirmation of crystal precipitation, heptane (60 mL) was dropwise added over about 15 minutes. The precipitated crystal was separated, washed with ethyl acetate-heptane (ethyl acetate:heptane=1:5, 3 mL) and dried to give the title compound (2.84 g, yield: 95%).

The melting start temperature of the crystal was 133.5° C.

EXAMPLE 5

The crystal (3.0 g, 8.12 mmol) of (R)-2-[[[3-methyl-4-(2,2,2-trifluoroethoxy)-2-pyridinyl]methyl]sulfinyl]-1H-benzimidazole was dissolved in ethyl acetate (12 mL) at about 50° C. The mixture was stirred at about 25° C. for about 2 hours, and after confirmation of crystal precipitation, hexane (24 mL) was dropwise added over about 20 minutes. The precipitated crystal was separated, washed with ethyl acetate-hexane (ethyl acetate:hexane=1:5, 3 mL) and dried to give the title compound.

The melting start temperature of the crystal was 133.5° C.

EXAMPLE 6

The crystal (2.0 g, 5.41 mmol) of (R)-2-[[[3-methyl-4-(2,2,2-trifluoroethoxy)-2-pyridinyl]methyl]sulfinyl]-1H-benzimidazole was dissolved in n-propyl acetate (30 mL) at about 30° C. The mixture was concentrated to 8 mL under reduced pressure at an outer temperature of about 25° C. After stirring for about 1.5 hours, crystal precipitation was confirmed, and heptane (16 mL) was dropwise added over about 20 minutes. The precipitated crystal was separated, washed twice with n-propyl acetate-heptane (n-propyl acetate:heptane=1:5, 6 mL) and dried to give the title compound (1.86 g, yield: 93%).

The melting start temperature of the crystal was 134.0° C.

EXAMPLE 7

The crystal (2.0 g, 5.41 mmol) of (R)-2-[[[3-methyl-4-(2,2,2-trifluoroethoxy)-2-pyridinyl]methyl]sulfinyl]-1H-benzimidazole was dissolved in i-propyl acetate (40 mL) at about 35° C. The mixture was concentrated to 8 mL under reduced pressure at an outer temperature of about 35° C. After stirring for about 1.5 hours, crystal precipitation was confirmed, and heptane (16 mL) was dropwise added over about 20 minutes. The precipitated crystal was separated, washed twice with i-propyl acetate-heptane (i-propyl acetate:heptane=1:5, 6 mL) and dried to give the title compound (1.89 g, yield: 95%).

The melting start temperature of the crystal was 133.0° C.

EXAMPLE 8

The crystal (2.0 g, 5.41 mmol) of (R)-2-[[[3-methyl-4-(2, 2,2-trifluoroethoxy)-2-pyridinyl]methyl]sulfinyl]-1H-benzimidazole was dissolved in n-butyl acetate (40 mL) at about 35° C. The mixture was concentrated to 8 mL under reduced pressure at an outer temperature of about 35° C. After stirring for about 1 hour, crystal precipitation was confirmed, and heptane (16 mL) was dropwise added over about 20 minutes. The precipitated crystal was separated, washed twice with n-butyl acetate-heptane (n-butyl acetate:heptane=1:5, 6 mL) and dried to give the title compound (1.87 g, yield: 93%).

The melting start temperature of the crystal was 133.0° C.

EXAMPLE 9

The crystal (2.0 g, 5.41 mmol) of (R)-2-[[[3-methyl-4-(2, 2,2-trifluoroethoxy)-2-pyridinyl]methyl]sulfinyl]-1H-benzimidazole was dissolved in methyl acetate (15 mL). The mixture was concentrated to 8 mL under reduced pressure at an outer temperature of about 25° C. After stirring for about 1.5 hours, crystal precipitation was confirmed, and heptane (16 mL) was dropwise added over about 20 minutes. The precipitated crystal was separated, washed twice with methyl acetate-heptane (methyl acetate:heptane=1:5, 6 mL) and dried to give the title compound (1.71 g, yield: 86%).

The melting start temperature of the crystal was 134.0° C.

EXAMPLE 10

The wet crystal obtained according to the method of the above-mentioned Reference Example 4 was dissolved in ethyl acetate (50 L). The mixture was partitioned and the organic layer was concentrated under reduced pressure until the liquid amount became about 27 L. Ethyl acetate (30 L) was added to the concentrate, and the mixture was concentrated under reduced pressure until the liquid amount became about 16 L. Ethyl acetate (30 L) and activated carbon (150 g) were added to the concentrate. The activated carbon was removed and the mixture was washed with ethyl acetate (1.5 L). The filtrate was concentrated under reduced pressure until the concentration of (S)-2-[[[3-methyl-4-(2,2, 2-trifluoroethoxy)-2-pyridinyl]methyl]sulfinyl]-1H-benzimidazole became about 0.27 g/mL (12.5 L). After stirring at about 25° C. for about 2 hours under a nitrogen gas stream, crystal precipitation was confirmed, and heptane (25 L) was dropwise added over about 1.5 hours. The mixture was stirred for about 1.5 hours. The precipitated crystal was separated, washed with ethyl acetate-heptane (ethyl acetate: heptane=1:5, 6 L) and dried to give the title compound (3.76 kg, yield: 72% based on 2-[[[3-methyl-4-(2,2,2-trifluoroethoxy)-2-pyridinyl]methyl]thio]-1H-benzimidazole).

As a result of the analysis of the crystal by X-ray powder diffraction, the crystal showed an X-ray powder diffraction analysis pattern having characteristic peaks at interplanar spacings(d) of 11.68, 6.77, 5.84, 5.73, 4.43, 4.09, 3.94, 3.89, 3.69, 3.41 and 3.11 Angstrom.

As a result of the analysis of the crystal by high performance liquid chromatography (conditions (A)), the enantiomeric excess of (S)-2-[[[3-methyl-4-(2,2,2-trifluoroethoxy)-2-pyridinyl]methyl]sulfinyl]-1H-benzimidazole in the crystal was 100% ee.

As a result of the analysis of the crystal by high performance liquid chromatography (conditions (B)), analogous materials in the crystal, such as sulfone, sulfide and the like were not found.

The melting start temperature of the crystal was 133.5° C.

EXAMPLE 11

The crystal (1.5 g, 4.06 mmol) of (R)-2-[[[3-methyl-4-(2, 2,2-trifluoroethoxy)-2-pyridinyl]methyl]sulfinyl]-1H-benzimidazole was dissolved in ethyl acetate (30 mL). The mixture was concentrated to 6 mL under reduced pressure at an outer temperature of about 25° C. The mixture was stirred for about 2 hours at the same temperature, and precipitation of the crystal was confirmed. Heptane (24 mL) was dropwise added over about 30 minutes. The mixture was stirred for about 2.5 hours, and the precipitated crystal was separated and dried to give the title compound (1.46 g, yield: 97.3%).

The melting start temperature of the crystal was 133.5° C.

Experimental Example: Stability Test (Relationship Between Melting Start Temperature and Stability)

Various (R)-lansoprazole crystals obtained in the above-mentioned Reference Examples and Examples were subjected to a stability test at 60° C. for one month. The partial results are shown in Table 1 below.

TABLE 1

| production method | melting start temperature | 60° C. one month residual ratio |
|---|---|---|
| present invention (1) (Example 2) | 135.0° C. | 100% |
| present invention (2) (Example 1) | 134.0° C. | 99.7% |
| present invention (3) (Example 6) | 134.0° C. | 99.2% |
| conventional method (A) (Reference Example 6) | 130.0° C. | 93.8% |
| conventional method (B) (Reference Example 3) | 127.5° C. | 89.8% |

The crystal obtained by the method of the present invention shows a residual ratio of not less than 99% in a 60° C. one month stability test. The crystal obtained by a conventional method shows a residual ratio decreased to about 90-94%.

The crystal of (R)-lansoprazole was subjected to a 40° C. one month stability test. The partial results are shown in the following Table 2.

TABLE 2

| production method | present invention (Example 11) | conventional method (Reference Example 7) |
|---|---|---|
| melting start temperature initial | 133.5° C. | 128.5° C. |
| appearance | almost white | almost white |
| content | 99.5% | 99.6% |
| analogous material content 40° C. one month | 0.2% | 0.1% |
| appearance | almost white | brown |
| content | 99.7% | 93.8% |
| analogous material content | 0.2% | 4.6% |

By the method of the present invention, decomposition was not found in the 40° C. one month stability test, but the appearance was degraded, the content decreased and the analogous material content increased by the conventional method.

Figure 1:
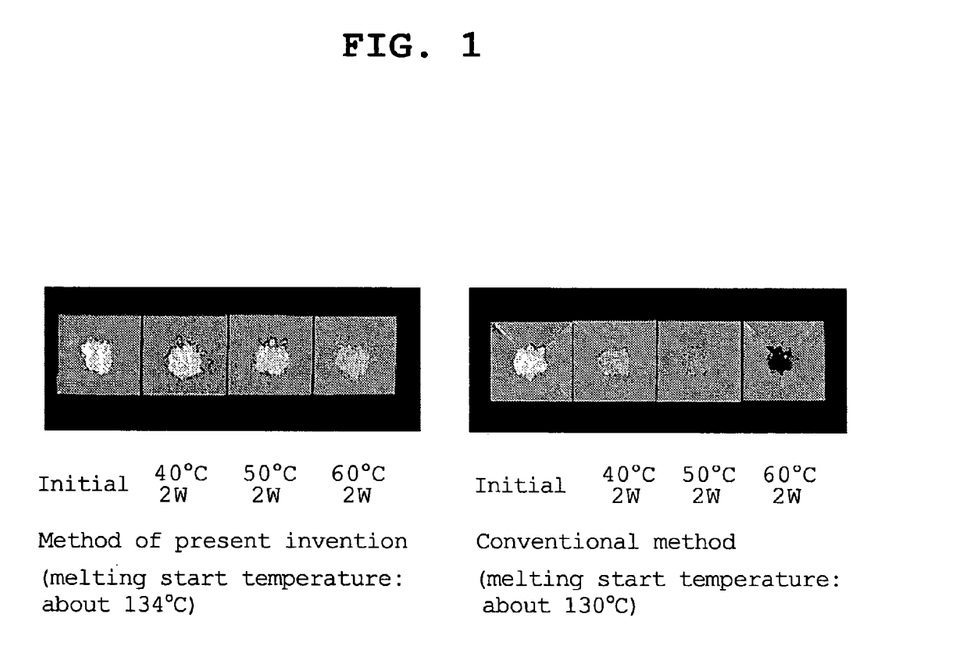
FIG. 1 shows the appearance of a crystal (Example 1) having a melting start temperature of about 134° C. and a crystal (Reference Example 6) having a melting start temperature of about 130° C., before stability test (initial) and after stability test at 40° C. for 2 weeks, 50° C. for 2 weeks and 60° C. for 2 weeks.

In FIG. 1, the appearance of a crystal (Example 1) having a melting start temperature of about 134° C. and a crystal (Reference Example 6) having a melting start temperature of about 130° C. before stability test and after stability tests (40° C. 2 weeks, 50° C. 2 weeks and 60° C. 2 weeks) is shown. The crystal having a melting start temperature of about 134° C. did not show changes in the appearance but the crystal having a melting start temperature of about 130° C. showed appreciably degraded appearance.

From the foregoing results, it is apparent that there exists a clear relationship between melting start temperature and stability in the case of the crystals of (R)-lansoprazole and (S)-lansoprazole, and that the crystal having a melting start temperature of not lower than about 131° C. is stable but the crystal having a melting start temperature of less than about 131° C. is unstable.

Formulation Example 1

Production of Capsule

Capsules (15 mg) were obtained according to the charge amount-1 in the following Table 3 and the following method (in Table 4, amounts per capsule are shown). (1) The crystal of (R)-2-[[[3-methyl-4-(2,2,2-trifluoroethoxy)-2-pyridinyl] methyl]sulfinyl]-1H-benzimidazole (hereinafter to be referred to as compound A) obtained in Example 1 and the ingredients (3) to (6) were thoroughly mixed to give a dusting powder. In a centrifugal fluidized coating granulator was charged (2) Nonpareil and the above-mentioned dusting powder was coated while spraying an aqueous solution of (7) hydroxypropyl cellulose in purified water. The spherical granules were dried in vacuo at 40° C. for 16-20 hours and passed through a sieve (600 μm, 1180 μm) to give base granules. The base granules were placed in a roll flow type coating machine and coated with a suspension of (8) methacrylic acid copolymer LD-(12) polysorbate 80 in purified water. The coated granules were passed through a sieve (710 μm, 1400 μm) and dried in vacuo at 40° C. for 16-20 hours to give enteric coated granules. To the enteric coated granules were added (13) talc and (14) light silicic anhydride and mixed granules were produced in a tumbler mixer. The mixed granules were filled in (17) HPMC Capsule No. 2 by a capsule filling machine to give 15 mg capsules.

By controlling the amount to be filled of the above-mentioned mixed granules, 20 mg and 10 mg capsules were produced.

TABLE 3

| | Charge amount-1 | |
|---|---|---|
| ingredients | | 15 mg capsule |
| [base granule] | | |
| (1) | compound A | 450.0 g |
| (2) | sucrose · starch spherical granule (Nonpareil) | 1650.0 |
| (3) | magnesium carbonate | 336.0 |
| (4) | purified sucrose | 897.0 |
| (5) | cornstarch | 546.0 |
| (6) | low-substituted hydroxypropyl cellulose | 600.0 |
| (7) | hydroxypropyl cellulose | 21.0 |
| | purified water | 1029.0 |
| | subtotal | 4500.0 g |
| [enteric coated granule] | | |
| | base granule | 3600.0 g |
| (8) | methacrylic acid copolymer LD (Eudragit L30D-55$^{TR}$) | 535.2 |
| (9) | talc | 160.8 |
| (10) | macrogol 6000 | 52.8 |
| (11) | titanium oxide | 52.8 |
| (12) | polysorbate 80 | 24.0 |
| | purified water | 2054.4 |
| | subtotal | 4425.6 g |
| [mixed granule] | | |
| | enteric coated granule | 3688.0 g |
| (13) | talc | 6.0 |
| (14) | light silicic anhydride | 2.0 |
| | subtotal | 3696.0 g |
| [capsule] | | |
| | mixed granule | 924.0 g |
| (15) | HPMC Capsule No. 2 | 5000.0 cap. |

TABLE 4

| | Formulation per capsule | |
|---|---|---|
| ingredients | | 15 mg capsule |
| [base granule] | | |
| (1) | compound A | 15.00 mg |
| (2) | sucrose · starch spherical granule (Nonpareil) | 55.00 |
| (3) | magnesium carbonate | 11.20 |
| (4) | purified sucrose | 29.90 |
| (5) | cornstarch | 18.20 |
| (6) | low-substituted hydroxypropyl cellulose | 20.00 |
| (7) | hydroxypropyl cellulose | 0.70 |
| | subtotal | 150.00 mg |
| [enteric coated granule] | | |
| | base granule | 150.00 mg |
| (8) | methacrylic acid copolymer LD (Eudragit L30D-55$^{TR}$) | 22.30 |
| (9) | talc | 6.70 |
| (10) | macrogol 6000 | 2.20 |
| (11) | titanium oxide | 2.20 |
| (12) | polysorbate 80 | 1.00 |
| | subtotal | 184.40 mg |

TABLE 4-continued

Formulation per capsule

| ingredients | | | 15 mg capsule |
|---|---|---|---|
| [mixed granule] | | | |
| (13) | | enteric coated granule | 184.40 mg |
| (14) | | talc | 0.30 |
|  | | light silicic anhydride | 0.10 |
|  | | subtotal | 184.80 mg |
| [capsule] | | | |
|  | | mixed granule | 184.80 mg |
| (15) | | HPMC Capsule No. 2 | 62.00 |
|  | | subtotal | 246.80 mg |

Formulation Example 2

Production of Capsule

Capsules (15 mg) were obtained according to the charge amount-2 in the following Table 5 and the following method (in Table 6, amounts per capsule are shown). (1) Compound A and the ingredients (3) to (6) were thoroughly mixed to give a main drug dusting powder. The ingredients (7) to (9) were thoroughly mixed to give a cover coating agent. In a centrifugal fluidized coating granulator was charged (2) Nonpareil and the above-mentioned main drug dusting powder and the cover coating agent were successively coated while spraying an aqueous solution of (10) hydroxypropyl cellulose in purified water. The spherical granules were dried in vacuo at 40° C. for 16-20 hours and passed through a sieve (600 μm, 1180 μm) to give base granules. The base granules were placed in a roll flow type coating machine and coated with a suspension of (11) methacrylic acid copolymer LD-(15) polysorbate 80 in purified water. The coated granules were passed through a sieve (710 μm, 1400 μm) and dried in vacuo at 40° C. for 16-20 hours to give enteric-coated granules. To the enteric coated granules were added (16) talc and (17) light silicic anhydride and mixed granules were produced in a tumbler mixer. The mixed granules were filled in (18) HPMC Capsule No. 2 by a capsule filling machine to give 15 mg capsules.

TABLE 5

Charge amount-2

| ingredients | | |
|---|---|---|
| [base granule] | | |
| (1) | compound A | 450.0 g |
| (2) | sucrose · starch spherical granule (Nonpareil) | 1650.0 |
| (3) | magnesium carbonate | 336.0 |
| (4) | purified sucrose | 597.0 |
| (5) | cornstarch | 300.0 |
| (6) | low-substituted hydroxypropyl cellulose | 354.0 |
| (7) | purified sucrose | 300.0 |
| (8) | cornstarch | 246.0 |
| (9) | low-substituted hydroxypropyl cellulose | 246.0 |
| (10) | hydroxypropyl cellulose | 21.0 |
|  | purified water | 1029.0 |
|  | subtotal | 4500.0 g |
| [enteric coated granule] | | |

TABLE 5-continued

Charge amount-2

| ingredients | | |
|---|---|---|
| (11) | base granule | 3600.0 g |
|  | methacrylic acid copolymer LD (Eudragit L30D-55$^{TR}$) | 535.2 |
| (12) | talc | 160.8 |
| (13) | macrogol 6000 | 52.8 |
| (14) | titanium oxide | 52.8 |
| (15) | polysorbate 80 | 24.0 |
|  | purified water | 2054.4 |
|  | subtotal | 4425.6 g |
| [mixed granule] | | |
|  | enteric coated granule | 3688.0 g |
| (16) | talc | 6.0 |
| (17) | light silicic anhydride | 2.0 |
|  | subtotal | 3696.0 g |
| [capsule] | | |
|  | mixed granule | 924.0 g |
| (18) | HPMC Capsule No. 2 | 5000.0 cap. |

TABLE 6

Formulation per capsule

| ingredients | | 15 mg capsule |
|---|---|---|
| [base granule] | | |
| (1) | compound A | 15.0 mg |
| (2) | sucrose · starch spherical granule (Nonpareil) | 55.0 |
| (3) | magnesium carbonate | 11.2 |
| (4) | purified sucrose | 19.9 |
| (5) | cornstarch | 10.0 |
| (6) | low-substituted hydroxypropyl cellulose | 11.8 |
| (7) | purified sucrose | 10.0 |
| (8) | cornstarch | 8.2 |
| (9) | low-substituted hydroxypropyl cellulose | 8.2 |
| (10) | hydroxypropyl cellulose | 0.7 |
|  | subtotal | 150.0 mg |
| [enteric coated granule] | | |
|  | base granule | 150.0 mg |
| (11) | methacrylic acid copolymer LD (Eudragit L30D-55$^{TR}$) | 22.3 |
| (12) | talc | 6.7 |
| (13) | macrogol 6000 | 2.2 |
| (14) | titanium oxide | 2.2 |
| (15) | polysorbate 80 | 1.0 |
|  | subtotal | 184.4 mg |
| [mixed granule] | | |
|  | enteric coated granule | 184.4 mg |
| (16) | talc | 0.3 |
| (17) | light silicic anhydride | 0.1 |
|  | subtotal | 184.8 mg |

TABLE 6-continued

| | Formulation per capsule | |
|---|---|---|
| ingredients | | 15 mg capsule |
| [capsule] | | |
| (18) | mixed granule | 184.8 mg |
| | HPMC Capsule No. 2 | 62.0 |
| | subtotal | 246.8 mg |

INDUSTRIAL APPLICABILITY

According to the production method of the present invention, a crystal of (R)-lansoprazole or (S)-lansoprazole superior in preservation stability can be produced efficiently on an industrial large scale.

This application is based on patent application No. 2000-367757 filed in Japan, the contents of which are hereby incorporated by reference.

The invention claimed is:

1. A method for producing a crystal of (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole, which comprises crystallizing at a temperature of about 0° C. to about 35° C. from a $C_{1-4}$ alkyl acetate solution containing (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole at a concentration of about 0.1 g/mL to about 0.5 g/mL.

2. A method for producing a crystal of (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole, which comprises crystallizing at a temperature of about 0° C. to about 35° C. from a $C_{1-4}$ alkyl acetate solution containing (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole at a concentration of about 0.1 g/mL to about 0.5 g/mL, and adding dropwise to the $C_{1-4}$ alkyl acetate solution, at the same temperature, $C_{5-8}$ hydrocarbon in an amount of not more than 7 times the amount of the $C_{1-4}$ alkyl acetate solution.

3. The method of claim 1, wherein the crystallization temperature is about 20° C. to about 30° C.

4. The method of claim 1, wherein the crystallization is conducted for about 30 minutes to about 4 hours.

5. The method of claim 1, wherein the $C_{1-4}$ alkyl acetate is ethyl acetate or propyl acetate.

6. The method of claim 2, wherein the $C_{5-8}$ hydrocarbon is added in an amount of not more than 5 times the amount of the $C_{1-4}$ alkyl acetate solution.

7. The method of claim 2, wherein the $C_{5-8}$ hydrocarbon is heptane or hexane.

8. The method of claim 2, wherein the $C_{5-8}$ hydrocarbon is added dropwise over about 15 minutes to about 4 hours.

9. A crystal of (R)-2-[[[3-methyl-4-(2,2,2-trifluoroethoxy)-2-pyridinyl]methyl]sulfinyl]-1H-benzimidazole or (S)-2-[[[3-methyl-4-(2,2,2-trifluoroethoxy)-2-pyridinyl]methyl]sulfinyl]-1H-benzimidazole having a melting start temperature of not lower than about 131° C.

10. The crystal of claim 9, wherein the melting start temperature is about 135° C.

11. The method of claim 2, wherein the crystallization temperature is about 20° C. to about 30° C.

12. The method of claim 2, wherein the crystallization is conducted for about 30 minutes to about 4 hours.

13. The method of claim 2, wherein the $C_{1-4}$ alkyl acetate is ethyl acetate or acetate.

* * * * *

UNITED STATES PATENT AND TRADEMARK OFFICE
CERTIFICATE OF CORRECTION

PATENT NO. : 7,285,668 B2  
APPLICATION NO. : 10/432798  
DATED : October 23, 2007  
INVENTOR(S) : Hashimoto et al.

Page 1 of 1

It is certified that error appears in the above-identified patent and that said Letters Patent is hereby corrected as shown below:

In the Claims:

Claim 13, column 30, line 36: delete "is ethyl acetate or acetate" and insert --is ethyl acetate or propyl acetate--.

Signed and Sealed this
Twelfth Day of August, 2014

Michelle K. Lee
*Deputy Director of the United States Patent and Trademark Office*